(12) United States Patent
Schermeier et al.

(10) Patent No.: US 8,210,178 B2
(45) Date of Patent: Jul. 3, 2012

(54) RESPIRATOR WITH A CARBON DIOXIDE ABSORBER

(75) Inventors: Olaf Schermeier, Lübeck (DE);
Jürgen-Ralf Lange, Hamberge (DE);
Heiko Lokotsch, Pokrent (DE); Brigitte Dautzenberg, Lübeck (DE)

(73) Assignee: Dräger Medical GmbH, Lübeck (DE)

( * ) Notice: Subject to any disclaimer, the term of this patent is extended or adjusted under 35 U.S.C. 154(b) by 957 days.

(21) Appl. No.: 11/423,221

(22) Filed: Jun. 9, 2006

(65) Prior Publication Data

US 2006/0278220 A1    Dec. 14, 2006

(30) Foreign Application Priority Data

Jun. 10, 2005    (DE) .......................... 10 2005 026 838

(51) Int. Cl.
*A62B 7/10*    (2006.01)
*A62B 23/02*    (2006.01)
*A62B 7/00*    (2006.01)
*A62B 9/00*    (2006.01)
*A62B 9/04*    (2006.01)

(52) U.S. Cl. ......... 128/205.28; 128/200.24; 128/202.22; 128/202.27; 128/205.23; 128/205.27

(58) Field of Classification Search ............. 128/202.22, 128/202.27, 204.21, 205.23, 205.28, 205.12, 128/205.27, 200.24, 207.14; 340/573.1, 340/572.7, 572.8, 693.5
See application file for complete search history.

(56) References Cited

U.S. PATENT DOCUMENTS

| | | | | |
|---|---|---|---|---|
| 4,440,162 A * | 4/1984 | Sewell et al. ............ | 128/202.22 |
| 4,994,117 A * | 2/1991 | Fehder ........................... | 436/133 |
| 5,674,381 A * | 10/1997 | Den Dekker .................... | 210/85 |
| 5,765,550 A * | 6/1998 | Psaros et al. ............. | 128/202.27 |
| 5,810,001 A * | 9/1998 | Genga et al. ............. | 128/202.27 |
| 6,360,742 B1 * | 3/2002 | Maxwell et al. ......... | 128/202.27 |
| 6,618,687 B2 * | 9/2003 | Warkander ..................... | 702/130 |
| 6,626,355 B2 * | 9/2003 | Sasse et al. .................. | 235/375 |
| 7,148,806 B2 * | 12/2006 | Anttila et al. .............. | 340/573.1 |
| 7,151,456 B2 * | 12/2006 | Godfrey ...................... | 340/573.1 |
| 7,191,777 B2 * | 3/2007 | Brand et al. ............. | 128/200.23 |
| 7,424,889 B2 * | 9/2008 | Mashak .................... | 128/205.28 |
| 7,520,566 B2 * | 4/2009 | Braun ............................ | 297/335 |
| 2005/0118048 A1 | 6/2005 | Traxinger | |
| 2005/0211761 A1 * | 9/2005 | Anttila et al. ................. | 235/376 |
| 2006/0231092 A1 * | 10/2006 | Mashak .................... | 128/200.23 |
| 2007/0215157 A1 * | 9/2007 | Straw ....................... | 128/205.12 |

FOREIGN PATENT DOCUMENTS

| | | |
|---|---|---|
| DE | 20113789 U1 | 6/2002 |
| EP | 0 769 304 A | 4/1997 |
| EP | 1 170 023 A | 1/2002 |
| WO | WO 2004033024 A | 4/2004 |
| WO | WO 2004040202 A | 5/2004 |
| WO | WO 2005118036 A | 12/2005 |

* cited by examiner

*Primary Examiner* — Annette Dixon

(74) *Attorney, Agent, or Firm* — McGlew and Tuttle, P.C.

(57) ABSTRACT

A respirator shall be improved concerning better utilization of the carbon dioxide absorber (3). To accomplish the object, a transponder (5), which contains data on the type of absorber, the period of use and the current state of consumption, is arranged at the carbon dioxide absorber (3). A transponder polling device (8) at the respirator (1) reads the data from the memory chip (6) and an updated state of consumption is calculated from data on the operation of the respirator and stored again in the memory chip (6).

20 Claims, 2 Drawing Sheets

RESPIRATOR WITH A CARBON DIOXIDE ABSORBER

CROSS REFERENCE TO RELATED APPLICATIONS

This application claims the benefit of priority under 35 U.S.C. §119 of German Patent Application DE 10 2005 026 838.2 filed Jun. 10, 2006, the entire contents of which are incorporated herein by reference.

FIELD OF THE INVENTION

The present invention pertains to a respirator (also known as ventilator) with a rapid action coupling and with a carbon dioxide absorber, which has a connection element complementary to the rapid action coupling.

BACKGROUND OF THE INVENTION

A medical device with a base unit and with auxiliary devices that can be connected to the base unit is known from DE 201 13 789 U1. The auxiliary devices are flexible tube systems, containers and functional elements, which are necessary for the operation of the medical device. A transponder, which contains data on the type of the auxiliary device and the manufacturer, is arranged on each of the auxiliary devices. These data are detected by a transponder polling device attached to the base unit. and it is also possible to store data on the memory chip of the transponder via the transponder polling device. Due to the transponders arranged at the auxiliary devices, the base unit knows at any point in time with which auxiliary devices it is equipped.

A carbon dioxide absorber is needed in rebreathing operation in medical devices from the area of the anesthesia respiration technique in order to remove the carbon dioxide breathed out by a patient from the breathing gas. Various embodiments of carbon dioxide absorbers are offered here. In one group of absorbers, the absorber housing is opened and breathing lime (Atemkalk—a mixture of calcium hydroxide and alkali phosphate) is filled in as a bulk material. The breathing lime is disposed of later after use and replaced with fresh breathing lime. Disposable absorbers, which are disposed of completely after use, are known as well.

The depletion is determined by visual reading of the color change of the breathing lime. Since the limit of the color change frequently cannot be recognized unambiguously, the depletion can be estimated only roughly. It is therefore common practice in prior-art devices to change the absorber or the breathing lime in the absorber according to a fixed cycle. However, the capacity of the breathing lime is therefore frequently utilized only partially, because the interval at which the replacement is performed is determined according to the most unfavorable mode of operation.

SUMMARY OF THE INVENTION

The basic object of the present invention is to improve a respirator concerning the utilization of the carbon dioxide absorber.

According to the invention, a respirator is provided with a rapid action coupling. A carbon dioxide absorber is provided with a connection element, which is complementary to the rapid action coupling. A transponder is provided at the carbon dioxide absorber. A memory chip is associated with the transponder. The memory chip contains data on the type, period of use and current state of consumption of the absorbent. A transponder polling device is provided at the respirator. The transponder polling device reads data from the memory chip and stores data that were obtained during the operation in the memory chip in the form of an updated state of consumption.

The advantage of the present invention is essentially that a carbon dioxide absorber arranged on the respirator has a transponder with a memory chip, on which a specification of the absorbent being used as well as the current state of consumption are stored. A transponder polling device provided at the respirator reads data from the memory chip, on the one hand, and calculates an updated state of consumption, which will again be stored in the memory chip, from the operating data of the respirator. For example, phases of readiness, during which little or no absorption of carbon dioxide takes place, or the duration of mechanical respiration can be detected as operating data. Since the updated state of consumption is stored again on the memory chip, the depletion of the absorbent can also be determined when the carbon dioxide absorber is connected to another respirator. The product life of the carbon dioxide absorber can thus be reconstructed and carbon dioxide absorbers that were stored for an excessively long time and are no longer fully suitable for use can be recognized. Besides the current state of consumption, it is useful to store the type of the absorber, the type of the breathing lime being used, the date of manufacture and the expiration date on the memory chip.

It is advantageous to also store additionally a manufacturer code on the memory chip. The manufacturer code is likewise detected by the transponder polling device and compared with a list of permissible manufacturers in an evaluating unit of the respirator. A release signal that makes possible the operation of the respirator is generated in case of agreement. It is thus achieved that only accessories of authorized suppliers can be connected to the respirator.

The data on the memory chip are advantageously evaluated only if the connection element of the carbon dioxide absorber has snapped completely into the rapid action coupling of the respirator. The antenna and the transmission power of the transponder polling device are designed for this such that the content of the memory chip can be read only if the carbon dioxide absorber has snapped in. A mechanical coding may additionally also be present between the connection element and the rapid action coupling in order for the absorber to be able to be introduced in a preferred position only to reduce interface tolerances. The data of the memory chip may be evaluated only if the connection element has snapped completely into the said rapid action coupling.

Data on the operation of the carbon dioxide absorber are advantageously determined from the breathing gas flow through the carbon dioxide absorber and the carbon dioxide concentration on the side on which the flow reaches the carbon dioxide absorber. The mode of respiration may additionally also be included in the calculation of the operating data. The degree of depletion of the absorber can be determined in the evaluating unit from the operating data and the specification of the breathing lime being used, such as type and lime volume and displayed on a display unit in the form of a percentage depletion of the absorber. A simplified display of the depletion of the absorber can be embodied with three light-emitting diodes. A green light-emitting diode indicates that the carbon dioxide absorber is ready to operate. A yellow light-emitting diode signals, by contrast, the imminent depletion of the absorber, and a red light-emitting diode is activated when the carbon dioxide absorber is no longer ready for use.

An exemplary embodiment of the present invention is shown in the drawings and will be explained in greater detail below. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

In the drawings:
FIG. 2 is a respirator according to FIG. 1 with the carbon dioxide absorber snapped in.

DESCRIPTION OF THE PREFERRED EMBODIMENTS

Figure 1:
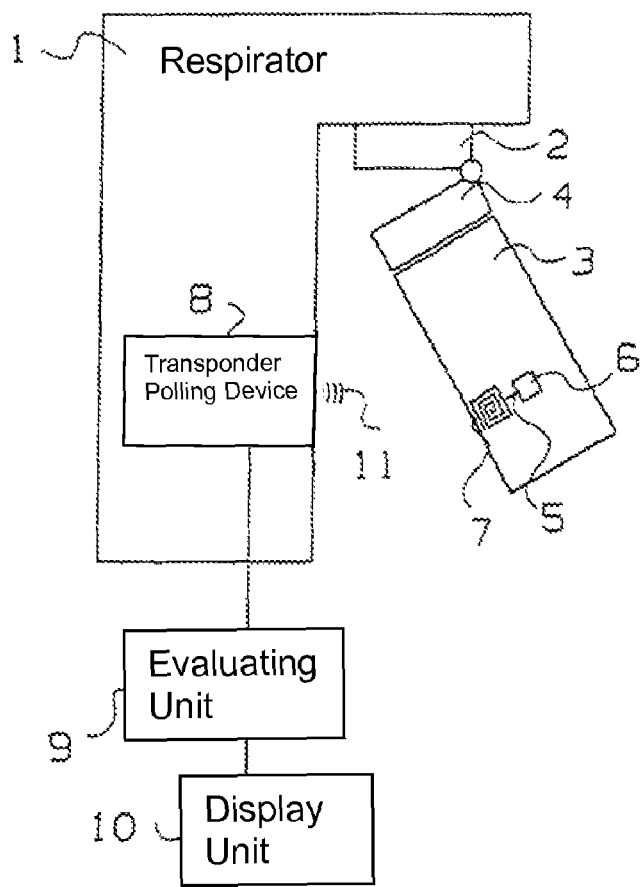
FIG. 1 is a respirator with a carbon dioxide absorber.

Referring to the drawings in particular, FIG. 1 schematically shows a respirator 1 with a rapid action coupling 2 for the connection of a carbon dioxide absorber 3. The carbon dioxide absorber 3 has a connection element 4, which is complementary to the rapid action coupling 2 and snaps into the rapid action coupling 2.

A transponder 5 with a memory chip 6 and with an antenna 7 are located at the carbon dioxide absorber 3. A transponder polling device 8 is connected to an evaluating unit 9 and a display unit 10. The transponder polling device 8 is attached to the respirator 1. The transponder polling device 8 can read both data of the memory chip 6 and write updated data on the memory chip 6.

The polling transmission is shown in FIG. 1 by lines 11. The range of the transponder polling device 8 is indicated by the extent of the lines 11.

Figure 2:
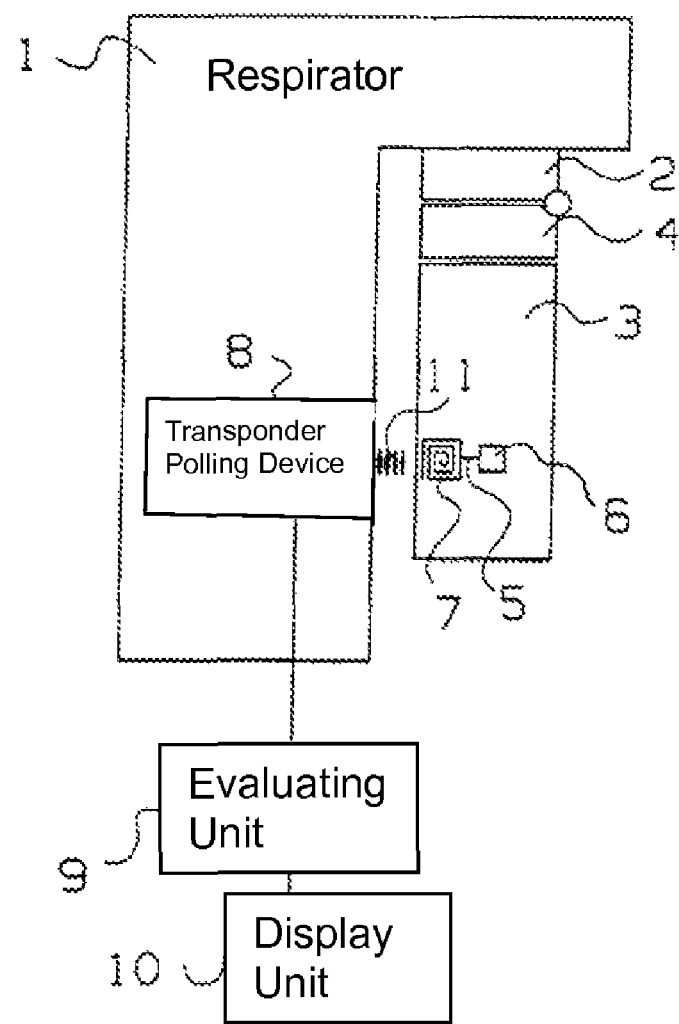

FIG. 2 shows the respirator 1 with the carbon dioxide absorber 3 snapped completely into the rapid action coupling 2. The antenna 7 of the transponder 5 now comes into the range of the polling transmission 11 of the transponder polling device 8.

The respirator according to the present invention operates as follows:

When the carbon dioxide absorber 3 is delivered, the type of absorber, the type of the breathing lime being used, a manufacturer code, the date of manufacture, the expiration date and the state of consumption are stored on the memory chip 6 of the transponder. The state of consumption, i.e., the depletion of the absorber, is 0% in the state as supplied and the period of use of the breathing lime is between the date of manufacture and the expiration date.

The connection element 4 of the carbon dioxide absorber 3 is introduced into the rapid action coupling 2 and it snaps in by turning, corresponding to FIGS. 1 and 2. The antenna 7 of the transponder 5 now comes into the reading range of the transponder polling device 8. The data of the memory chip 6 are now read first into the evaluating unit 9. The manufacturer code is compared there with a list of approved manufacturer codes in a first step. After a favorable conclusion, a check is performed to determine whether the expiration date has not yet been exceeded, and a release signal that makes possible the operation of the respirator 1 is then generated.

From sensors (e.g., sensor providing volume rate of flow data or other flow characteristics), which are not specifically shown, the evaluating unit 9 continuously receives data on the breathing gas flow through the carbon dioxide absorber 3 as well as data on the carbon dioxide concentration on the side on which the flow arrives at the carbon dioxide absorber 3, and the breathing mode set. The evaluating unit 9 calculates from this an updated state of consumption, e.g., 20%, and stores this again in the memory chip 6 together with a device code of the respirator 1. The current state of consumption of the carbon dioxide absorber 3 is provided as an output in the form of a bar graph display via the display unit 10. The product life of the carbon dioxide absorber 3 can be monitored without interruption with the data on the memory chip 6.

While specific embodiments of the invention have been shown and described in detail to illustrate the application of the principles of the invention, it will be understood that the invention may be embodied otherwise without departing from such principles.

What is claimed is:

1. A respirator comprising:
a respirator housing with a rapid action coupling;
a carbon dioxide absorber with absorbent and with a connection element, which is complementary to said rapid action coupling, said connection element being pivotably connected to said rapid action coupling such that said carbon dioxide absorber moves from a disconnected position to a connected position, said carbon dioxide absorber being in communication with said respirator housing in said connected position, said connection element engaging said rapid action coupling in said connected position, said carbon dioxide absorber not being in communication with said respirator housing in said disconnected position;
a transponder at said carbon dioxide absorber;
a memory chip associated with said transponder, said memory chip containing data on the type, period of use and current state of consumption of said absorbent, said memory chip being arranged at said carbon dioxide absorber; and
a transponder polling device at said respirator housing, said transponder polling device having a polling transmission range, said transponder being within said polling transmission range with said carbon dioxide absorber in said connected position, said transponder being located outside of said polling transmission range with said carbon dioxide absorber in said disconnected position, said transponder polling device reading data from said memory chip and storing data obtained during operation again in said memory chip in the form of an updated state of consumption with said carbon dioxide absorber in said connected position.

2. A respirator in accordance with claim 1, further comprising:
a display unit for displaying the updated state of consumption in the form indicating a depletion of said absorber.

3. A respirator in accordance with claim 1, further comprising an evaluating unit wherein a manufacturer code is additionally stored on said memory chip and said manufacturer code is received by said transponder polling device and is compared with a list of approved manufacturer codes in said evaluating unit and a release signal is generated in case of agreement of said manufacturer code stored on said memory chip and one of said list of approved manufacturer codes, the release signal making possible the operation of the respirator.

4. A respirator in accordance with claim 3, wherein said evaluating unit receives data on operation of the respirator, said data being obtained from the breathing gas flow through the carbon dioxide absorber and the carbon dioxide concentration on the side on which the flow reaches said carbon dioxide absorber.

5. A respirator in accordance with claim 1, wherein data of said memory chip is evaluated only if said connection element has snapped completely into said rapid action coupling, wherein said transponder polling device does not poll data from said memory chip with said connection element not snapped completely into said rapid action coupling, at least a portion of said carbon dioxide absorber being located at a first distance from said respirator housing in said connected position, said at least said portion of said carbon dioxide absorber being located at a second distance from said respirator housing with said carbon dioxide absorber in said disconnected position, said second distance being greater than said first distance.

6. A respirator system in accordance with claim 1, wherein said transponder is positioned opposite said transponder polling device in said connected position.

7. A respirator in accordance with claim 1, wherein said carbon dioxide absorber has a bottom portion, said bottom portion being located at a first distance from said respirator when said carbon dioxide absorber is in said connected position, said bottom portion being located at a second distance from said respirator when said carbon dioxide absorber is in said disconnected position, said first distance being less than said second distance, wherein at least a portion of said carbon dioxide absorber is movable in a direction toward said respirator and in a direction away from said respirator, said rapid action coupling having a longitudinal rapid action coupling axis, said carbon dioxide absorber having a carbon dioxide absorber longitudinal axis, said carbon dioxide absorber longitudinal axis being substantially aligned with said longitudinal rapid action coupling axis with said carbon dioxide absorber in said connected position, said carbon dioxide absorber longitudinal axis being offset at an angle with respect to said longitudinal rapid action coupling axis with said carbon dioxide absorber in said disconnected position.

8. A respirator in accordance with claim 1, wherein said respirator housing has a side surface, said transponder polling device being arranged at said side surface, said carbon dioxide absorber being parallel to said side surface when said carbon dioxide absorber is in said connected position.

9. A respirator system comprising:
a respirator with a rapid action coupling, said rapid action coupling having a rapid action coupling surface;
a carbon dioxide absorber with absorbent and a connection element, which is complementary to said rapid action coupling, said connection element having a connection element surface, said connection element being pivotably connected to said rapid action coupling such that said carbon dioxide absorber moves between a respirator connected position and a respirator disconnected position, said carbon dioxide absorber being in communication with said respirator in said respirator connected position, said rapid action coupling surface being in contact with said connection element surface in said respirator connected position;
a transponder at said carbon dioxide absorber;
a memory chip associated with said transponder, said memory chip containing data on the type, period of use and current state of consumption of said absorbent; and
a transponder polling device at said respirator, said transponder polling device having a data receiving and data transmitting range, at least a portion of said carbon dioxide absorber being located within said data receiving and data transmitting range in said respirator connected position, said transponder polling device reading data from said memory chip and storing data obtained during operation again in said memory chip in the form of an updated state of consumption with said carbon dioxide absorber in said respirator connected position, said transponder polling device not reading data or transmitting data to said memory chip with said carbon dioxide absorber in said respirator disconnected position.

10. A respirator system in accordance with claim 9, further comprising:
a display unit for displaying the updated state of consumption in the form indicating a depletion of said absorber.

11. A respirator system in accordance with claim 9, further comprising:
an evaluating unit wherein a manufacturer code is additionally stored on said memory chip and said manufacturer code is received by said transponder polling device and is compared with a list of approved manufacturer codes in said evaluating unit and a release signal is generated in case of agreement, the release signal making possible the operation of the respirator.

12. A respirator system in accordance with claim 11, wherein said evaluating unit receives data on operation of the respirator, said data being obtained from a breathing gas flow through the carbon dioxide absorber and a carbon dioxide concentration on the side on which the flow reaches said carbon dioxide absorber.

13. A respirator system in accordance with claim 9, wherein data of said memory chip is evaluated only if said connection element has snapped completely into said rapid action coupling, wherein said transponder polling device does not poll data from said memory chip with said connection element not snapped completely into said rapid action coupling, at least a portion of said carbon dioxide absorber being located at a first distance from said respirator housing in said first position, said at least said portion of said carbon dioxide absorber being located at a second distance from said respirator housing in said second position, said second distance being greater than said first distance, said connection element surface being arranged at an angle with respect to said rapid action coupling surface with said carbon dioxide absorber in said respirator connected position.

14. A respirator system in accordance with claim 9, wherein said transponder is positioned opposite said transponder polling device in said respirator connected position.

15. A respirator system in accordance with claim 9, wherein said carbon dioxide absorber has a bottom portion, said bottom portion being located at a first distance from said respirator when said carbon dioxide absorber is in said respirator connected position, said bottom portion being located at a second distance from said respirator when said carbon dioxide absorber is in said respirator disconnected position, said first distance being less than said second distance, said rapid action coupling having a longitudinal rapid action coupling axis, said carbon dioxide absorber having a carbon dioxide absorber longitudinal axis, said carbon dioxide absorber longitudinal axis being substantially aligned with said longitudinal rapid action coupling axis with said carbon dioxide absorber in said respirator connected position, said carbon dioxide absorber longitudinal axis being angularly offset with respect to said longitudinal rapid action coupling axis with said carbon dioxide absorber in said respirator disconnected position.

16. A respirator system comprising:
a respirator with a rapid action coupling, said rapid action coupling having a rapid action coupling surface, said respirator having a side surface;
a carbon dioxide absorber with absorbent and a connection element, which is complementary to said rapid action coupling, said connection element having a connection element surface, said connection element being pivotably connected to said rapid action coupling via a hinge connection such that said carbon dioxide absorber moves between a respirator contacting position and a respirator non-contacting position, said carbon dioxide absorber being in communication with said respirator in said respirator contacting position, said carbon dioxide absorber not being in communication with said respirator in said respirator non-contacting position, said rapid action coupling surface being in contact with said connection element surface in said respirator contacting position, said rapid action coupling surface being located at a spaced location from said rapid action coupling surface in said respirator non-contacting position;

a transponder at said carbon dioxide absorber;

an evaluating unit;

a memory chip associated with said transponder, said memory chip containing data on the type, period of use and current state of consumption of said absorbent, wherein data of said memory chip is evaluated via said evaluating unit only if said absorber is in said respirator contacting position; and a transponder polling device at said side surface of said respirator, said transponder polling device reading data from said memory chip and storing data obtained during operation again in said memory chip in the form of an updated state of consumption with said carbon dioxide absorber in said respirator contacting position, said transponder and said memory chip being located opposite said transponder polling device in said respirator contacting position, said carbon dioxide absorber being parallel to said side surface of said respirator with said carbon dioxide absorber in said respirator contacting position, said transponder polling device having a polling transmission range, said transponder being within said polling transmission range with said carbon dioxide absorber in said respirator contacting position, said transponder being located outside of said polling transmission range when said carbon dioxide absorber is in said respirator non-contacting position.

17. A respirator system in accordance with claim 16, further comprising:
a display unit for displaying the updated state of consumption in the form indicating a depletion of said absorber.

18. A respirator system in accordance with claim 16, wherein a manufacturer code is additionally stored on said memory chip and said manufacturer code is received by said transponder polling device and is compared with a list of approved manufacturer codes in said evaluating unit and a release signal is generated in case of agreement, the release signal making possible the operation of the respirator.

19. A respirator system in accordance with claim 16, wherein data on operation of the respirator is obtained from a breathing gas flow through the carbon dioxide absorber and a carbon dioxide concentration on the side on which the flow reaches said carbon dioxide absorber.

20. A respirator system in accordance with claim 16, wherein said carbon dioxide absorber has a bottom portion, said bottom portion being located at a first distance from said respirator when said carbon dioxide absorber is in said respirator contacting position, said bottom portion being located at a second distance from said respirator when said carbon dioxide absorber is in said respirator non-contacting position, said first distance being less than said second distance, said rapid action coupling having a longitudinal rapid action coupling axis, said carbon dioxide absorber having a carbon dioxide absorber longitudinal axis, said carbon dioxide absorber longitudinal axis being substantially aligned with said longitudinal rapid action coupling axis with said carbon dioxide absorber in said respirator contacting position, said carbon dioxide absorber longitudinal axis being angularly offset with respect to said longitudinal rapid action coupling axis with said carbon dioxide absorber in said respirator non-contacting position, said connection element surface being arranged at an angle with respect to said rapid action coupling surface with said carbon dioxide absorber in said respirator non-contacting position.

* * * * *